United States Patent [19]

Martinez et al.

[11] Patent Number: 5,417,105
[45] Date of Patent: May 23, 1995

[54] FLOW ACCELERATOR FOR LEAK DETECTOR PROBE

[75] Inventors: Erasmo Martinez, Torrace; Steven E. Walmsley, Signal Hill; Shu-Ming Chang, Monterey Park, all of Calif.

[73] Assignee: Hughes Aircraft Company, Los Angeles, Calif.

[21] Appl. No.: 198,245

[22] Filed: Feb. 18, 1994

[51] Int. Cl.$^6$ .................... G01N 1/24; G01M 3/04
[52] U.S. Cl. .................... 73/40.7; 73/863.58; 73/864.73
[58] Field of Search .............. 73/40.7, 863.41, 863.51, 73/863.58–864.33, 864.73–864.81

[56] References Cited

U.S. PATENT DOCUMENTS

| | | | |
|---|---|---|---|
| 3,771,349 | 11/1973 | Yatabe | 73/40.7 |
| 4,060,001 | 11/1977 | Archerd | 73/863.58 |
| 4,962,673 | 10/1990 | Wang et al. | 73/864.73 |
| 4,970,905 | 11/1990 | McClennen et al. | 73/864.73 |
| 5,281,397 | 1/1994 | Ligon et al. | 73/864.81 |

Primary Examiner—Hezron E. Williams
Assistant Examiner—Michael J. Brock
Attorney, Agent, or Firm—Georgann S. Grunebach; Wanda Denson-Low; Michael W. Sales

[57] ABSTRACT

A leak detection system (50) including a flow accelerator for directing and accelerating leaking gas toward a sampling probe (70). A probe input tube (72) is inserted into one end (62B) of a larger diameter adapter tube (60) to position the end of the tube (72) past a suction opening (62D). The other end (62A) of the adapter tube is positioned to receive leaking gas. A suction is applied to the suction opening, which tends to draw the leaking gas into the adapter tube end (62A). Some of the leaking gas is drawn into the suction opening, and some into the end of the sampling tube. The suction causes the leaking gas to be accelerated toward the sampling probe input port. The suction can be created by a venturi (66C) through which is passed a gas under pressure. The acceleration of the gas through the venturi creates the suction. The flow accelerator significantly reduces the time required to locate small gas leaks.

15 Claims, 2 Drawing Sheets

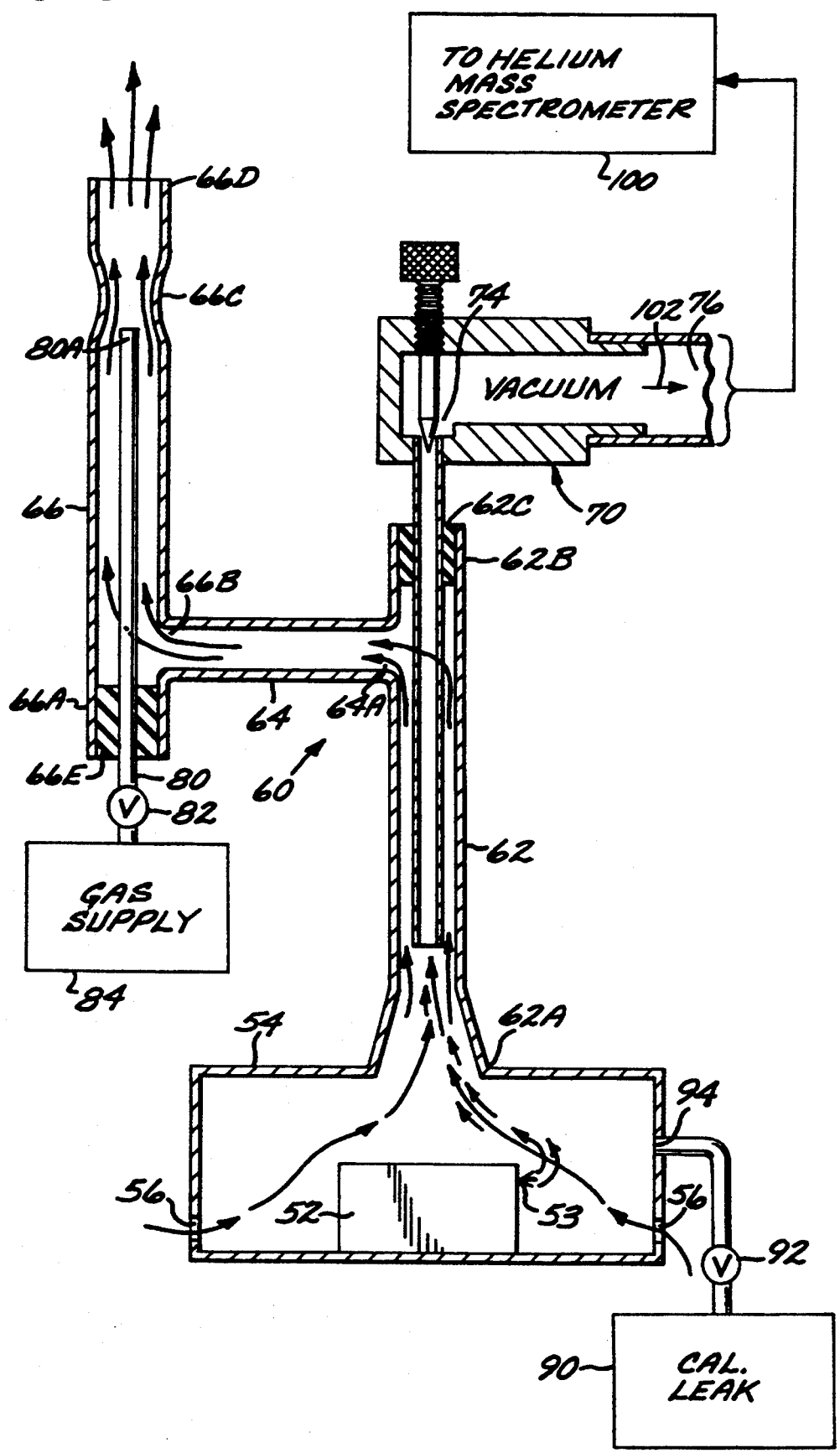

FLOW ACCELERATOR FOR LEAK DETECTOR PROBE

FIELD OF THE INVENTION

The present invention relates to apparatus for detecting gas leaks, and more particularly to such apparatus employing a nozzle to direct and accelerate leaking gas toward a sampling probe.

BACKGROUND OF THE INVENTION

In some applications, the total "out-leakage" of a large pressurized system must be accurately measured. The method used to measure this type of leakage with a mass spectrometer leak detector is called accumulation testing. The vessel to be tested is pressurized with a trace gas and placed in a sealed room with a leak detector and probe, or the instrument can be outside and the probe connected to the chamber through a port or opening. Any leakage of trace gas from the pressurized vessel will then be picked up by the detector. Since the concentration of trace gas in the room will be increasing with time, the output reading will also increase with time. The accumulation technique may be applied to the vessels of any size or configuration capable of being pressurized at greater than atmospheric pressure.

A conventional apparatus for accumulation testing is shown in FIG. 1. The free volume shown in FIG. 1 should be minimized where possible. This is recommended in order to reduce the time required to accumulate sufficient trace gas in the free volume for detection.

For the purpose of estimating the quantity of gas that accumulates the following relationship may be used:

$$P = Qt/V$$

where

Q = leak rate of gas into free volume leak rate specification.
V = free volume.
P = pressure change in free volume.
t = elapsed time of gas leakage (Q) into free volume.

The system can be calibrated in the following manner. Connect a standard leak in a manner that will allow the gas to leak into the free volume of the system.

1. Record the leak detector output versus time for the standard leak in a manner that will allow the gas to leak into the free volume of the system.
2. After the calibration data has been acquired, close or remove standard leak from system, purge free volume of trace gas if necessary and pressurize the test vessel with trace gas.
3. Record the leak detector output versus time for the item under test. When this data has been secured the total out-leakage may be compared and/or calculated from the standard calibration data.
4. The unknown leakage may be calculated from the following expression:

$$t_1 \times \frac{LR_1}{output_1} = t_2 \times \frac{LR_2}{output_2}$$

where $t_1$ = time for change in output when standard leak is valved into free volume
$LR_1$ = standard leak rate
$Output_1$ = net output for standard leak during $t_1$
$t_2$ = time for change in output when test port pressurized
$LR_2$ = unknown leak rate
$Output_2$ = net output as indicated during $t_2$ A sampling probe used with a leak detector operates by continually extracting small amounts of gas from the volume being sampled. This extraction is performed via a vacuum applied within the probe. Because the differential pressure between the sampling probe and the lead detector needs to be maintained, the flow through the probe must be restricted. Thus, the sampling probe must be moved very slowly when attempting to locate leaks. Likewise, when attempting to detect gross leaks from a test item within a non-evacuated enclosure, it can take several hours for the reading on the leak detector to stabilize. Furthermore, the repeatability is not consistent.

SUMMARY OF THE INVENTION

A leak detection system is described, which includes a sampling probe having an input port and an output port, and an input port at an end of a probe tube. A leak detection apparatus is connected to the sampling probe output port; the leak detection apparatus may be a helium mass spectrometer, for example.

In accordance with the invention, a flow accelerator for directing and accelerating gasses toward the sampling probe input port is provided. The flow accelerator includes an adaptor tube having a probe end and a gas input end, with an inner diameter larger than an outer diameter of the probe tube. The probe tube is inserted into a probe end of the adaptor tube so that the probe input port is disposed at an intermediate position within the adaptor tube.

The flow accelerator further includes means for applying suction to a suction opening in the adaptor tube between the probe end and the probe input port, thereby drawing gasses into the adaptor tube at the gas input end, and directing and accelerating the flow of gas into the probe input port. In an exemplary embodiment, the means for applying suction includes a sidearm tube having a first end in communication with the suction opening and a second end, and a flow accelerator tube having a first end and a second end, the flow accelerator tube having a nominal tube diameter at the first and second ends and having a region of narrowed tube diameter at a tube restriction region between the first and second ends, thereby creating a venturi. The sidearm tube second opening is connected to a sidearm opening in the flow accelerator tube between the venturi and the flow accelerator tube first end, thereby providing a gas flow path between the suction opening in the adaptor tube and the flow accelerator tube sidearm opening. An end of a gas supply tube having a smaller diameter than the nominal diameter of the flow accelerator tube is inserted into the first end of the flow accelerator tube to position the supply tube first end at the venturi. Gas is supplied under pressure through the supply tube to the venturi, where the gas is accelerated through the venturi, creating a gas suction at the sidearm opening.

BRIEF DESCRIPTION OF THE DRAWING

These and other features and advantages of the present invention will become more apparent from the following detailed description of an exemplary embodiment thereof, as illustrated in the accompanying drawings, in which:

FIG. 3 is a cross-section view of the system of FIG. 2.

DETAILED DESCRIPTION OF THE PREFERRED EMBODIMENT

The invention employs a nozzle type apparatus used to direct and accelerate leaking gas towards a sampling probe. When this device is used in conjunction with a leak detector, the amount of time required to locate small gas leaks is significantly reduced. Additionally, when used with an enclosure, the flow accelerator and probe can be used to rapidly and accurately measure the total leakage of the pressurized unit within the enclosure.

Figure 1:
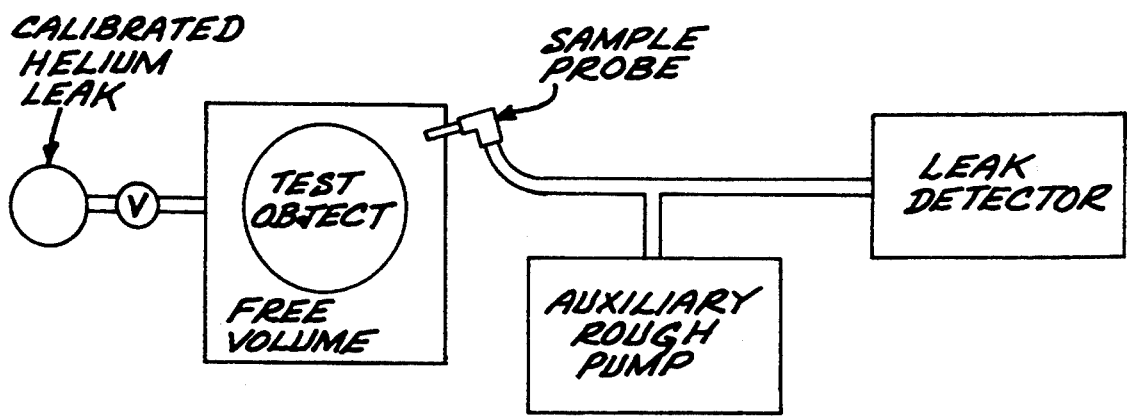
FIG. 1 is a block diagram of a conventional test setup for accumulation testing of the leakage of a large pressurized system.
Figure 2:
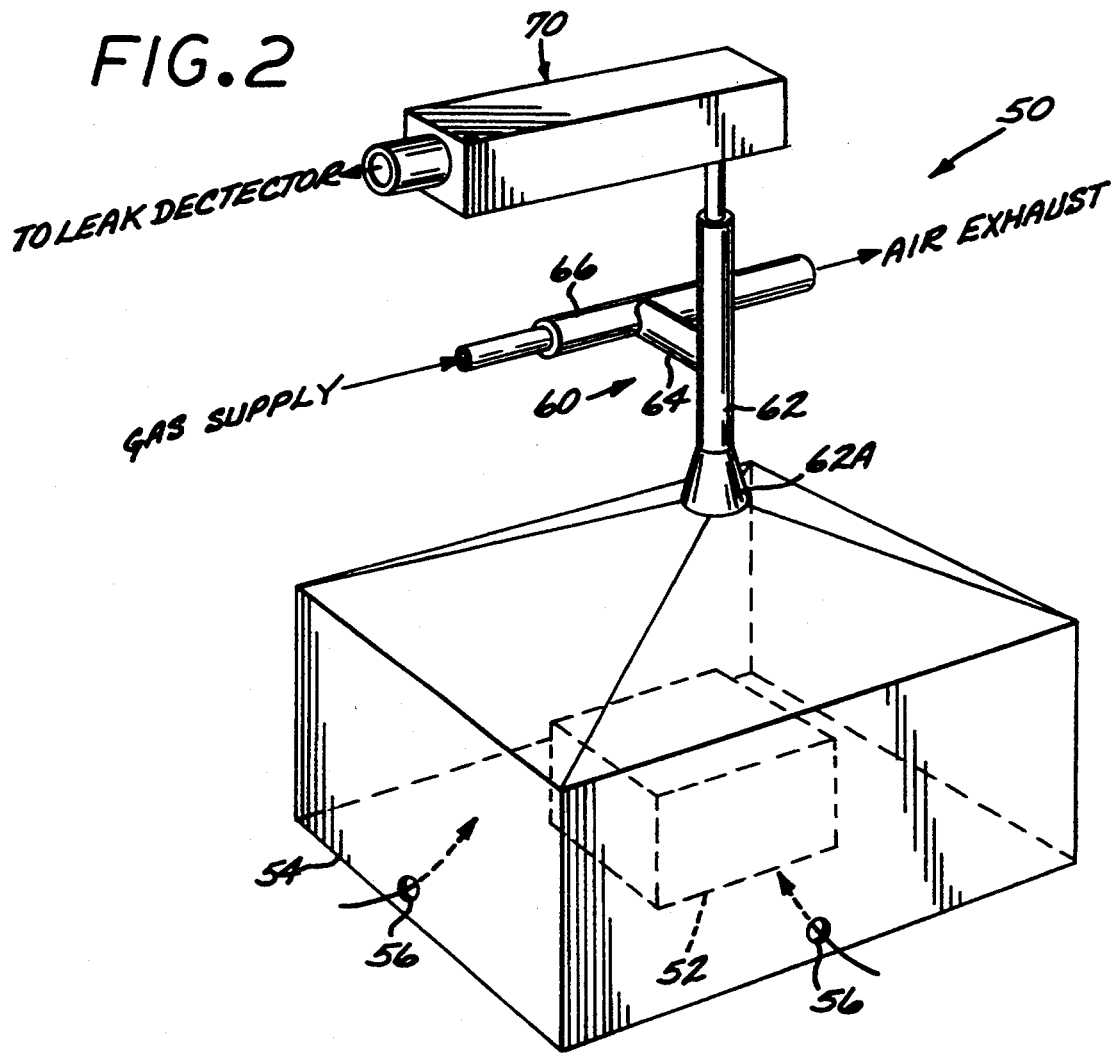
FIG. 2 is an isometric, partially broken away drawing of a leak detector system embodying the invention.

FIGS. 2 and 3 illustrate a leak detection system 50 employing a flow accelerator 60 for a leak detector sampling probe 70 in accordance with the present invention. The pressurized unit 52 under test is placed within an enclosure 54. The enclosure 54 has a number of vent holes 56 formed therein, and an opening 58 to which the sampling probe 70 is coupled via the flow accelerator 60. A calibrated leak source 90 is coupled to an opening 94 in the enclosure via a valve 92. This provides a means of performing a calibration of the leak detection system. Once the system has been calibrated, the unit under test is pressurized with a trace gas, and any leaks such as at location 53 can be measured to determine the leak rate.

The sampling probe 70 is itself conventional, and has a needle valve 74 to control the input opening size. The output port 76 of the probe 70 is connected to a conventional leak detector 100, e.g., a helium mass spectrometer. As in a conventional leak detection system, a vacuum indicated by arrow 102 is applied to draw gasses into the input port of the probe and into the leak detector.

The flow accelerator 60 comprises an adaptor tube 62 having an end 62A which opens into the opening 58 of the enclosure 54. The first end has a first diameter. The adaptor tube 62 also includes a second end opposing the first end. The probe tube 72 is inserted into the second end of the adaptor tube a considerable distance past a sidearm port opening 62D formed in the adaptor tube 62. A seal 62C provides a gas leak proof seal between the walls of the adaptor tube 62 and the probe tube 72. The sidearm 64 extends at a right angle to the adaptor tube 62, providing a transition to the flow accelerator tube 66, in turn extending orthogonally to the sidearm tube 64. The sidearm tube has an inner diameter of the same inner diameter as the inner diameter of the adaptor tube, in this exemplary embodiment.

The flow accelerator tube 66 has a first end 66A into which is inserted an gas supply tube capillary 80, with the end 80A extending well past the opening 66B to the sidearm tube 64 to a region 66C of narrowed diameter of the tube 66. The capillary tube in an exemplary implementation has an inner diameter of $\frac{1}{8}$ inch and an outer diameter of $\frac{1}{4}$ inch; the flow accelerator tube 66 has an exemplary nominal inner diameter of $\frac{3}{8}$ inches. A seal 66E provides a gas leak proof seal between the capillary tube and the flow accelerator tube end. The diameter of the tube 66 opens up to the nominal tube diameter at end 66D. Thus, a venturi is created at region 66C. The end 80B of the gas supply tube is connected to a gas supply source 84 through a valve 82.

The gas supply 84 in this exemplary embodiment provides a supply of low moisture nitrogen to the leak detection apparatus 50, under pressure on the order of 1 to 1 $\frac{1}{4}$ psi. Air has significant humidity, and moisture will condense at the venturi and freeze to clog the venturi. Other gasses could alternatively be used, e.g., air, so long as the gas is filtered and dried. The gas pressure of the gas supply 84 is proportional to the volume of the enclosure 54; the bigger the enclosure the higher the pressure needed to keep the measurement time small.

As a result of the venturi operation, a low pressure is created on the sidearm opening port 66D, drawing gas indicated by arrow 64A into the sidearm 64 through the adaptor tube 62 from the opening 62A in the enclosure. The venture effect also accelerates the flow of gas from the tube 62 into the sampling probe 70. The gas from the source 84 and drawn from the enclosure through tube 66 is exhausted at end 66D of the flow accelerator tube.

One purpose of this invention is to utilize the flow accelerator suction apparatus with the sampling probe to accelerate, direct, and stabilize the flow of the leaking tracer gas towards the sampling probe. The leaking tracer gas source, e.g., helium, is from the calibrated leak 90 during the system calibration mode of operation, and from the unit 52 under test during the actual test. The advantages are a significant reduction in the amount of time required for the sampling probe to detect a tracer gas, and consistent repeatability. Thus, a sampling probe can be moved rapidly along areas of suspected leakage when attempting to locate leak sources, instead of measuring leak rates as illustrated in the embodiment of FIGS. 2 and 3. When the system is to be used as a leak locator, the purpose is not to measure precisely the quantity of gas leaking, but rather to pinpoint the location at which the gas is leaking. In this case, the end 62A of the adaptor tube 62 is not secured to an enclosure 54, but is free to be moved with the sampling probe along areas of suspected leakage. In this case, the sampling probe can be connected to the leak detector 100 via a length of flexible tubing, and/or the adaptor tube 62 can be a flexible tube. The end 62A of the adaptor tube can then be moved through areas of suspected leakage to locate a leak. A cup can be mounted to the end 62A to protect against windy conditions interfering with the detection. While it is known to use a cup at the input port of the sampling probe during leak detection operations, the accelerator apparatus permits a larger cup to be used, thereby increasing the gas collection rate in a localized area. To pinpoint the leak after its general location has been determined with the aid of the flow accelerator, the accelerator tube 62 can be removed from the sampling probe tube 72, and the tube 72 used to precisely locate the leak.

When attempting to detect gross leaks from test items within a non-evacuated enclosure, test times are dramatically reduced. Previously, stabilized readings for a small leak ($2 \times 10^{-2}$ to $2 \times 10^{-4}$ cc/sec, in test items pressurized from 4 to 10 psig, inside a one cubic foot non-evacuated enclosure) varied from two to three hours depending on the shape of the test item and the amount of pressurization. With the flow accelerator employed with the sampling probe, repeatable readings are obtained within five to six minutes. Leak tests on the test items having leaks within the range of $2 \times 10^{-2}$ to $2 \times 10^{-4}$ cc/sec and pressurization of 4 to 10 psig can be performed with greatly reduced time, and with the same accuracy as an evacuated enclosure.

It is understood that the above-described embodiments are merely illustrative of the possible specific embodiments which may represent principles of the present invention. Other arrangements may readily be devised in accordance with these principles by those skilled in the art without departing from the scope and spirit of the invention.

What is claimed is:

1. A leak detection system, comprising:
   a sampling probe having an input port and an output port;
   a leak detection apparatus connected to said sampling probe output port; and
   flow acceleration means for directing and accelerating gasses toward said sampling probe input port, said means comprising an adaptor tube having a gas input end and a probe end disposed adjacent said sampling probe, and means for applying suction to a suction opening in said adaptor tube, thereby drawing gasses into said adaptor tube at said gas input end and directing and accelerating the flow of gas toward said sampling probe and into said sampling probe input port.

2. The system of claim 1 wherein said sampling probe includes a probe tube, and wherein said sampling probe input port is at an end of said probe tube, and said probe tube is inserted through said probe end of said adaptor tube so that said suction opening is disposed between sampling probe input port and said adaptor tube probe end.

3. The system of claim 1 wherein said means for applying suction at said suction opening comprises:
   a sidearm tube having a first end in communication with said suction opening and a second end;
   a flow accelerator tube having a first end and a second end, said flow accelerator tube having a nominal tube diameter at said first and second ends and having a region of narrowed tube diameter at a tube restriction region between said first and second ends, thereby creating a venturi;
   said sidearm tube second opening is connected to a sidearm opening in said flow accelerator tube between said venturi and said flow accelerator tube first end, thereby providing a gas flow path between said suction opening in said adaptor tube and said flow accelerator tube sidearm opening;
   a gas supply tube having a smaller diameter than said nominal diameter of said flow accelerator tube, said gas supply tube having a first end and a second end, wherein said gas supply tube is inserted into said first end of said flow accelerator tube to position said supply tube first end at said venturi; and
   a gas supply connected to said gas supply tube second end to provide gas under pressure through said gas supply tube to said supply tube first end, wherein said gas is accelerated through said venturi region, creating a gas suction at said sidearm opening.

4. The system of claim 3 wherein said gas is supplied by said gas supply at a pressure under two pounds per square inch.

5. The system of claim 3 wherein said gas provided under pressure is nitrogen.

6. The system of claim 3 wherein said gas provided under pressure is dried to prevent said venturi from clogging due to freezing moisture at said venturi.

7. A leak detection system, comprising:
   a sampling probe tube having an input port and an output port, said input port at an end of said sampling probe tube;
   a leak detection apparatus connected to said sampling probe tube output port; and
   flow acceleration means for directing and accelerating gasses toward said sampling probe tube input port, said means comprising an adaptor tube having a probe end and a gas input end, said adaptor tube having an inner diameter larger than an outer diameter of said sampling probe tube, said sampling probe tube being inserted into said probe end of said adaptor tube so that said sampling probe tube input port is disposed at an intermediate position within said adaptor tube, and means for applying suction to a suction opening in said adaptor tube between said adaptor tube probe end and said sampling probe tube input port, thereby drawing gasses into said adaptor tube at said gas input end and directing and accelerating the flow of gas into said sampling probe tube input port.

8. The leak detection system of claim 7 wherein said means for applying suction at said suction opening comprises:
   a sidearm tube having a first end in communication with said suction opening and a second end;
   a flow accelerator tube having a first end and a second end, said flow accelerator tube having a nominal tube diameter at said first and second ends and having a region of narrowed tube diameter at a tube restriction region between said first and second ends, thereby creating a venturi;
   said sidearm tube second end is connected to a sidearm opening in said flow accelerator tube between said venturi and said flow accelerator tube first end, thereby providing a gas flow path between said suction opening in said adaptor tube and said flow accelerator tube sidearm opening;
   a gas supply tube having a smaller diameter than said nominal diameter of said flow accelerator tube, said gas supply tube having a first end and a second end, wherein said gas supply tube is inserted into said first end of said flow accelerator tube to position said supply tube first end at said venturi; and
   a gas supply connected to said gas supply tube second end to provide gas under pressure through said gas supply tube to said supply tube first end, wherein said gas is accelerated through said venturi region, creating a gas suction at said sidearm opening.

9. The system of claim 8 wherein said gas is supplied by said gas supply at a pressure under two pounds per square inch.

10. The system of claim 8 wherein said gas provided under pressure is nitrogen.

11. The system of claim 8 wherein said gas provided under pressure is dried to prevent said venturi from clogging due to freezing moisture at said venturi.

12. A flow acceleration apparatus for directing and accelerating the flow of gasses toward a leak detection device, comprising:
   an adaptor tube having a gas input end and an output end disposed adjacent the leak detection device; and
   means for applying suction to a suction opening in said adaptor tube, thereby drawing gasses into said adaptor tube at said gas input end and directing and accelerating the flow of gas toward said leak detection device at said output end, said means for applying suction at said suction opening comprising:
a sidearm tube having a first end in communication with said suction opening and a second end;
a flow accelerator tube having a first end and a second end, said flow accelerator tube having a nominal tube diameter at said first and second ends and having a region of narrowed tube diameter at a tube restriction region between said first and second ends, thereby creating a venturi;
wherein said sidearm tube second end is connected to a sidearm opening in said flow accelerator tube between said venturi and said flow accelerator tube first end, thereby providing a gas flow path between said suction opening in said adaptor tube and said flow accelerator tube sidearm opening;
a gas supply tube having a smaller diameter than said nominal diameter of said flow accelerator tube, said gas supply tube having a first end and a second end, wherein said gas supply tube is inserted into said first end of said flow accelerator tube to position said supply tube first end at said venturi; and
a gas supply connected to said gas supply tube second to provide gas under pressure through said gas supply tube to said supply tube first end, wherein said gas is accelerated through said venturi region, creating a gas suction at said sidearm opening.

13. The apparatus of claim 12 wherein said gas is supplied by said gas supply at a pressure under two pounds per square inch.

14. The system of claim 12 wherein said gas provided under pressure is nitrogen.

15. The system of claim 12 wherein said gas provided under pressure is dried to prevent said venturi from clogging due to freezing moisture at said venturi.

* * * * *